(12) United States Patent
Kuhn et al.

(10) Patent No.: US 8,758,827 B2
(45) Date of Patent: *Jun. 24, 2014

(54) LOCAL SYSTEM FOR THE RELEASE OF ACTIVE PRINCIPLE AND PROCESS FOR ITS MANUFACTURE

(75) Inventors: Klaus-Dieter Kuhn, Marburg-Elnhausen (DE); Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/949,260

(22) Filed: Nov. 18, 2010

(65) Prior Publication Data

US 2011/0062637 A1    Mar. 17, 2011

Related U.S. Application Data

(62) Division of application No. 11/620,172, filed on Jan. 5, 2007, now abandoned.

(30) Foreign Application Priority Data

Feb. 10, 2006 (DE) .......................... 10 2006 006 510

(51) Int. Cl.
*A61K 9/50* (2006.01)

(52) U.S. Cl.
USPC ............................ 424/497; 424/489; 424/501

(58) Field of Classification Search
None
See application file for complete search history.

(56) References Cited

U.S. PATENT DOCUMENTS

| | | | | |
|---|---|---|---|---|
| 3,882,858 A | * | 5/1975 | Klemm | ........................... 606/76 |
| 4,233,287 A | | 11/1980 | Heysser et al. | |
| 5,286,791 A | * | 2/1994 | DeNicola et al. | ............... 525/71 |
| 6,160,033 A | | 12/2000 | Nies | |

FOREIGN PATENT DOCUMENTS

| | | |
|---|---|---|
| DE | 23 20 373 A1 | 11/1974 |
| DE | 26 51 441 A1 | 5/1978 |
| DE | 196 41 775 A1 | 2/1998 |
| GB | 1 560 017 A | 1/1980 |
| GB | 2 285 924 A | 8/1995 |
| WO | 99/21595 A | 5/1999 |

OTHER PUBLICATIONS

European Search Report Dated May 24, 2012.

\* cited by examiner

*Primary Examiner* — James Rogers
(74) *Attorney, Agent, or Firm* — Norris McLaughlin & Marcus PA

(57) ABSTRACT

A local system for the release of active principle is described which consists of approximately spherical or rotation symmetrical bodies which are composed essentially of polymethyl methacrylate or polymethyl methacrylate co-methyl acrylate, zirconium dioxide or barium sulphate and one or more pharmaceutical active principles, in particular antibiotics, and which are produced by radical polymerization, radical polymerization activators effective in the temperature range of 10-80° C. or residues of these polymerization activators from the groups of aromatic amines, heavy metal salts and barbiturates not being contained therein.

A process for the production of the local system for the release of active principle in the case of which a) a paste is produced by mixing methyl methacrylate, polymethyl methacrylate or polymethyl methacrylate co-methyl acrylate, zirconium dioxide and/or barium sulphate, one or more pharmaceutical active principles and a thermally decomposing radical initiator, the paste having a viscosity such that it cannot be deformed at room temperature by the effect of gravity;

b) the paste is injection molded by an injection molding device without heating at room temperature into approximately spherical or rotation-symmetrical bodies or the approximately spherical or rotation symmetrical bodies are injection-molded onto a wire;

c) the bodies are heated to a temperature at which the polymerization initiator decomposes.

5 Claims, No Drawings

LOCAL SYSTEM FOR THE RELEASE OF ACTIVE PRINCIPLE AND PROCESS FOR ITS MANUFACTURE

This is a Division of application Ser. No. 11/620,172, filed Jan. 5, 2007, now abandoned.

The object of the invention is a locally effective system for the release of active principle which system consists of approximately spherical or rotation symmetrical bodies which are composed essentially of polymethyl methacrylate or polymethyl methacrylate co-methyl acrylate, zirconium dioxide or barium sulphate and one or more pharmaceutical active principles.

One of the major challenges in bone surgery is even today posed by the treatment of osteomyelitis. Osteomyelitis can be hematogenous, post-traumatic or postoperative. Particularly difficult to treat is the chronic form of osteomyelitis which, in extreme cases, can lead to the loss of limbs and even to septicaemia.

A common method is surgical remediation by radical surgical debridement. During this procedure, the infected or necrotic bone is excised extensively. Subsequently, the bone cavity is filled with a local carrier of antibiotics or treated by repeated rinse-suction drainage. As a result of the local release of large quantities of antibiotics, the bacterial germs remaining in the adjacent bone areas, too, are effectively controlled when using a sufficiently bone-accessible bactericidal antibiotic such as gentamicin sulphate and clindamycin hydrochloride.

Spherical local systems for the release of active principle composed of polymethyl methacrylate, zirconium dioxide and an antibiotic were described for the first time by Klaus Klemm in 1975 (DE 23 20 373). This concept proved to be basically successful although it had the disadvantage that only a small part of the active principle contained in the spheres was released.

As a further development of this active principle carrier, it was proposed by Heuser and Dingeldein in 1978, to add glycine or other amino acids to improve the release of the antibiotic (DE 26 51 441). Following contact with the discharge from the wound, the incorporated amino acids are dissolved and form pore systems from which the active principle is able to diffuse out. In this way an improved release of active principle is achieved.

Local systems for the release of active principle composed mainly of polymethyl methacrylate, an opaquer for x-ray beams and an antibiotic can be produced either by a special injection moulding process (DE 23 20 373) or by casting antibiotic-containing polymethyl methacrylate bone cements in special moulds (EP 796 712). Injection moulding has the crucial disadvantage that temperatures of >120° C. are required in order to melt the polymer. As a result, it is not possible to integrate thermally labile antibiotics or other thermally labile active principles into these local systems for the release of active principles. As a result, the system for the release of active principle charged with gentamicin, which is produced by conventional injection moulding, has been the only one to be available on the market under the name of Septopal®. Gentamicin is an antibiotic which is extremely thermally stable. In view of the increasing spread of resistant and, in particular, multi-resistant bacteria, however, further antibiotics are desirable in local systems for the release of active principle. Unfortunately, these antibiotics, such as vancomycin and teicoplanin are thermally unstable. As a result, it has not been possible so far to produce local systems for the release of active principle with these antibiotics by injection moulding.

An alternative in this respect is suggested in EP 796 712, according to which it is possible to produce implant materials using thermally labile active principles. During this process, a conventional PMMA bone cement is mixed with one or several antibiotics and transferred into corresponding moulds made of plastic, for example. Conventional PMMA bone cements consist of a powder component—composed of a polymer powder, an opaquer for x-ray beams and a polymerisations initiator—and a liquid monomer component containing methyl methacrylate, a stabilisator and a polymerisation activator. After mixing both components, the polymerisation activator and the polymerisation initiator meet each other and radical polymerisation of the methyl methacrylate is initiated. After a few minutes, the PMMA bone cement has been cured. As a result of this curing behaviour, it is possible to produce chain-type systems for the release of active principle by means of the moulds proposed in EP 796 712 by using conventional PMMA bone cements only in a batchwise process. Continuous production under industrial conditions is consequently not possible. In the case of this manufacturing process, N,N-dimethyl-p-toluidine is used as polymerisation activator in the PMMA bone cement.

The invention is based on the object of developing a locally effective system for the release of active principle which can be produced continuously. The production process is to make it possible to integrate also thermally labile antibiotics into the systems for the release of active principle. The disadvantages of the processes described in DE 23 20 373 and EP 796 712 are to be overcome.

The object has been achieved by developing a local system for the release of active principle which system consists of spherical bodies which are composed essentially of polymethyl methacrylate or polymethyl methacrylate co-methyl acrylate, zirconium dioxide or barium sulphate and a pharmaceutical active principle and which are produced by radical polymerisation, radical polymerisation activators effective in the temperature range of 10-80° C. or residues of such polymerisation activators, in particular from the groups of aromatic amines, heavy metal salts and barbiturates not being contained therein.

In particular, the system for the release of active principle according to the invention does not contain N,N-dimethyl aniline, N,N-dimethyl-p-toluidine, N,N,-bis-hydroxyethyl-p-toluidine or their consequential products formed during the initiation of radical polymerisation.

The invention also relates to a process for the production of the local active principle system in the case of which a) a paste is produced by mixing methyl methacrylate, polymethyl methacrylate or polymethyl methacrylate co-methyl acrylate, zirconium dioxide and/or barium sulphate, one or more pharmaceutical active principles and a thermally decomposing radical initiator, the paste having a viscosity such that it is not deformed at room temperature by the effect of gravity;

b) the paste is injection moulded by an injection moulding device without heating at room temperature into approximately spherical or rotation symmetrical bodies or the approximately spherical or rotation symmetrical bodies are injection-moulded onto a wire;

c) the bodies are heated to a temperature at which the polymerisation initiator decomposes.

Heating can be effected e.g. by the effect of infrared radiation or by the effect of hot air or by the effect of microwaves.

It is important for the bodies produced from the paste to be mechanically stable before curing to such an extent that these are not deformed as a result of their inherent mass by the effect of gravity or, if the bodies are injection-moulded onto threads, become detached from the threads.

Thermally decomposing radical initiators which the expert would consider as commonly used are in particular those from the group consisting of dibenzoyl peroxide, dilauroyl peroxide and azoisobutyrodinitrile.

In step b) a wire is preferably used which is preheated to a temperature in the region of the decomposition temperature of the thermal initiator. By preheating the wire it is possible to initiate polymerisation in the interior of the injection moulded body before curing is effected by the effect of infrared radiation, hot air or by microwaves. As a result, the bodies adhere in a particularly stable manner on the wire.

The injection moulding tool is preferably made of Teflon or another inert plastic.

The invention will be explained by the following examples though without restricting the invention.

EXAMPLE 1

A paste of 570.0 g of polymethyl methacrylate co-methyl acrylate (molecular weight ~800,000 g/mole), 285.0 g of methyl methacrylate, 89.0 g of zirconium dioxide, 42.0 g of gentamicin sulphate (AK 600), 8.8 g of a mixture of dibenzoyl peroxide and water in a weight ratio of 3:1 and 15.0 g of glycine is produced by intense mixing. Using this viscous paste, approximately spherical bodies with a diameter of 7 mm are injection moulded by means of an injection moulding device on a polyfilic, surgical steel wire. The injection moulding process takes place at room temperature. Subsequently, the bodies are hardened in a dryer tunnel at a temperature of 80° C. The bodies formed have a mass of ~240 mg.

EXAMPLE 2

A paste of 570.0 g of polymethyl methacrylate co-methyl acrylate (molecular weight ~800,000 g/mole), 285.0 g of methyl methacrylate, 89.0 g of zirconium dioxide, 45.0 g of vancomycin hydrochloride, 8.8 g of a mixture of dibenzoyl peroxide and water in a weight ratio of 3:1 and 15.0 g of glycine is produced by intense mixing. Using the paste formed, approximately spherical bodies with a diameter of 7 mm are injection moulded by means of an injection moulding device on a polyfilic, surgical steel wire. Immediately afterwards, the bodies are hardened continually with a heating radiator while the injection-moulded bodies are heated to 60-70° C. by the effect of IR radiation and polymerisation is initiated. The cured bodies have a mass of ~240 mg.

We claim:

1. Process for the production of a local system for the release of an active principle which consists of spherical or rotationally symmetrical bodies which are composed essentially of
   i) polymethyl methacrylate and polymethyl methacrylate co-methyl acrylate,
   ii) zirconium dioxide and/or barium sulphate, and
   iii) one or more pharmaceutically active principles, said local system not containing radical polymerization activators which are effective in the temperature range of 10-80° C. selected from the group consisting of aromatic amines, heavy metal salts and barbiturates, or residues thereof, by local polymerization, which comprises
   a) producing a paste by mixing
      methyl methacrylate,
      optionally polymethyl methacrylate,
      polymethyl methacrylate co-methyl acrylate,
      zirconium dioxide and/or barium sulphate,
      one or more pharmaceutical active principles, and
      a thermally decomposing radical initiator,
      the paste having a viscosity sufficient to prevent deformation at room temperature by the effect of gravity;
   b) injection moulding the paste by an injection moulding device into spherical or rotationally symmetrical bodies or injection moulding spherical or rotationally-symmetrical bodies onto a wire;
   c) heating the bodies to a temperature at which the thermally decomposing radical initiator decomposes and polymerizing the methyl methacrylate.

2. Process according to claim 1, wherein in step c) heating is by infrared radiation, hot air or microwaves.

3. Process according to claim 1, wherein the decomposing radical initiator is one or more of the substances selected from the group consisting of dibenzoyl peroxide, dilauroyl peroxide and azoisobutyrodinitrile.

4. Process according to claim 1, wherein in step b) a wire is used which is preheated to a temperature in the region of the decomposition temperature of the thermally decomposing radical initiator.

5. Process according to claim 1, wherein the injection moulding device is made of polytetrafluoroethylene or another inert plastic.

* * * * *